United States Patent [19]
Jenkins, Jr.

[11] Patent Number: 5,613,969
[45] Date of Patent: Mar. 25, 1997

[54] TIBIAL OSTEOTOMY SYSTEM

[76] Inventor: Joseph R. Jenkins, Jr., 12203 Becontree Dr., Baton Rouge, La. 70810

[21] Appl. No.: 384,856

[22] Filed: Feb. 7, 1995

[51] Int. Cl.⁶ ............................................. A61B 17/15
[52] U.S. Cl. ....................................... 606/87; 606/88
[58] Field of Search ........................... 606/86, 87, 88, 606/89, 96, 97, 98

[56] References Cited

U.S. PATENT DOCUMENTS

| | | | |
|---|---|---|---|
| 2,570,465 | 10/1951 | Lundholm | 606/73 |
| 4,421,112 | 12/1983 | Mains et al. | |
| 4,952,213 | 8/1990 | Bowman et al. | 606/79 |
| 5,021,056 | 9/1989 | Hofmann et al. | 606/86 |
| 5,053,039 | 10/1991 | Hofmann et al. | 606/87 |
| 5,246,444 | 9/1993 | Schreiber | 606/87 |

*Primary Examiner*—Stephen C. Pellegrino
*Assistant Examiner*—Scott B. Markow
*Attorney, Agent, or Firm*—Warner J. Delaune

[57] ABSTRACT

A surgical kit for performing a tibial osteotomy is provided, comprising a pair of mounting pins for attaching, an osteotomy guide in a predetermined relation to a tibia; an osteotomy guide, comprising a transverse slot, defining a transverse cutting plane, adapted to receive and guide a transverse cutting blade for making a transverse cut into the tibia, and a plurality of oblique slots angularly offset from the transverse slot, each oblique slot defining an oblique cutting plane, adapted to receive and guide an oblique cutting blade for making a selected oblique cut into the tibia, wherein the intersection of each oblique cutting plane with the transverse cutting plane defines a wedge of bone which may be removed from the tibia. Also included with the surgical kit are a compression clamp adapted to apply compressive forces to a first portion of the tibia above the transverse cut and to a second portion of the tibia below the oblique cut to draw the first and second portions together, and a fixation plate adapted to hold the portions of the tibia together during healing. A method for performing an upper tibial osteotomy is also provided which employs the osteotomy surgical kit.

12 Claims, 6 Drawing Sheets

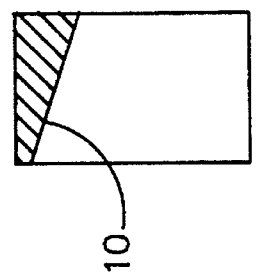
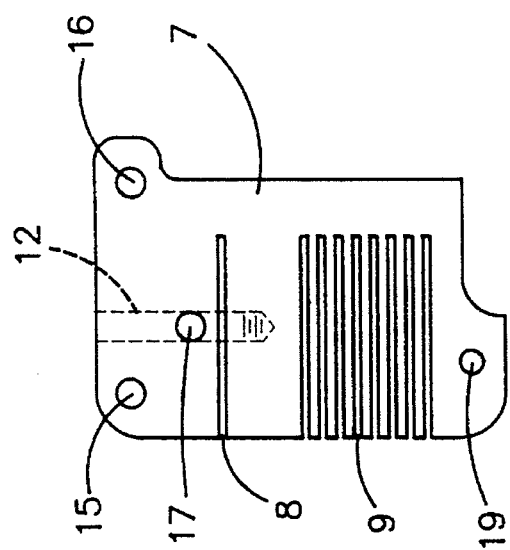
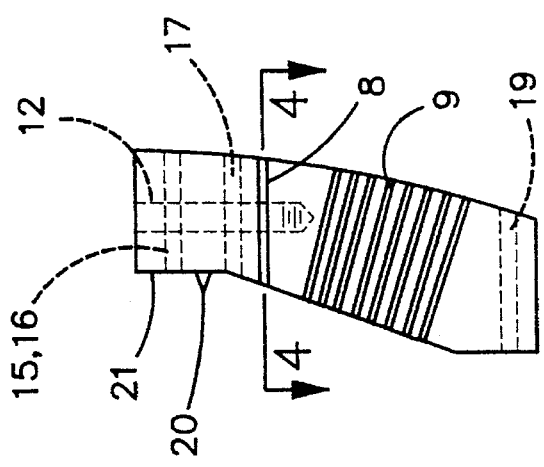
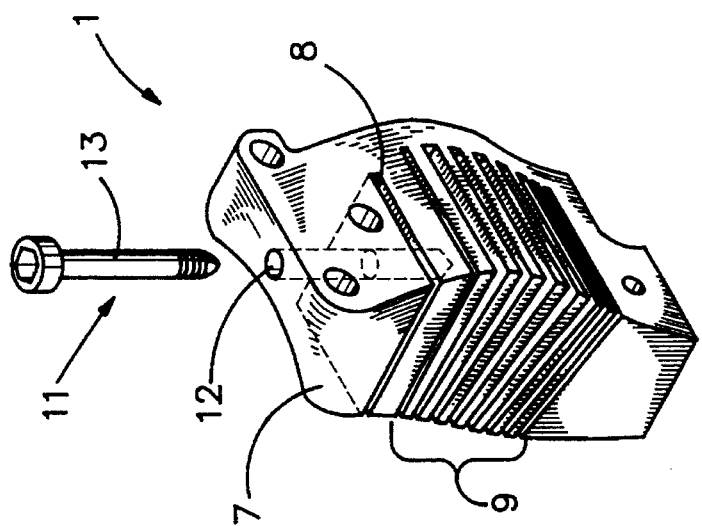

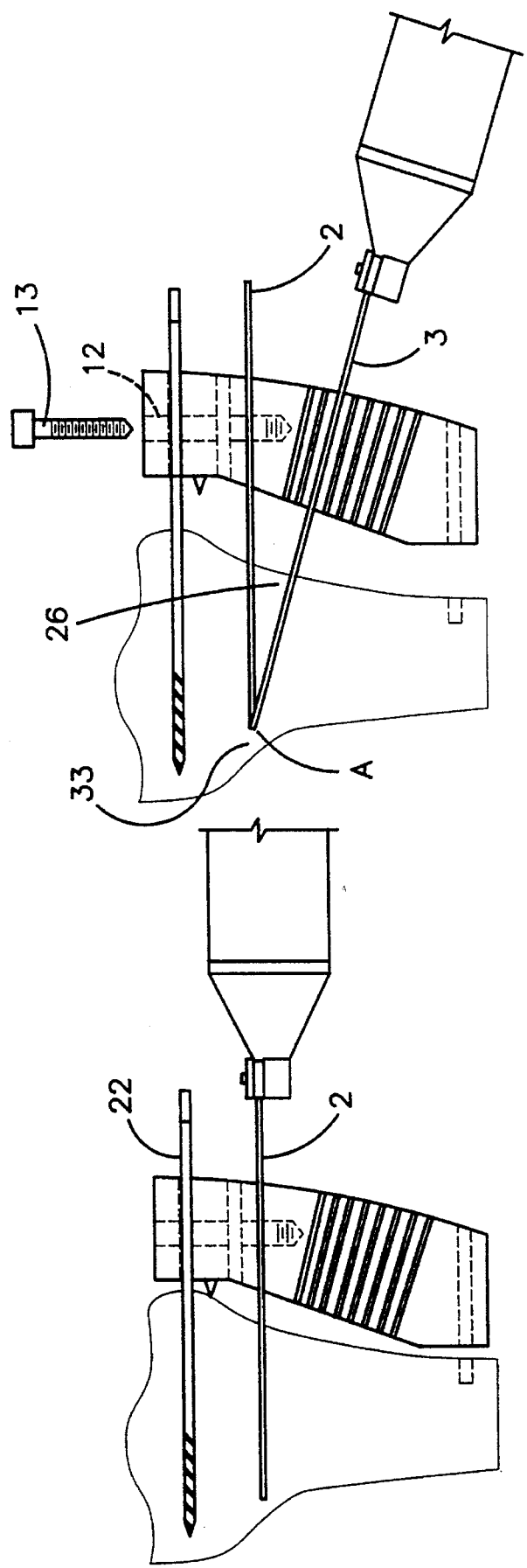

TIBIAL OSTEOTOMY SYSTEM

BACKGROUND OF THE INVENTION

I. Field of the Invention

The present invention relates generally to devices and methods for removing bone, and more particularly to such devices and methods used in performing tibial osteotomies in humans.

II. Description of Prior Art

Many devices have been developed over the years to facilitate the removal of bone from the leg in order to correct certain malalignments of the legs. Malalignment of the anatomical axis and the mechanical axis along the tibia and femur in the coronal plane can lead to degenerative osteoarthritis of the knee. The abnormal loading stresses caused by such malalignment can be quite painful, and corrective surgery is often required to place the anatomical axes of the tibia and femur in proper alignment. The most common surgical procedure employed to correct tibiofemoral malalignment is the upper tibial osteotomy, which removes a wedge-shaped portion from the cancellous bone of the metaphysis of the tibia. The size of the wedge to be removed is determined by the surgeon upon an analysis of the gait of the patient, the degree of tibiofemoral malalignment, the patient's indication of the precise location of pain, and several other factors. After the wedge is removed, the head and distal portions of the tibia are slowly pulled toward one another to close the resultant gap. When the gap is closed, a bracket is used to keep the internal bone surfaces together until the surgical wound is properly healed. Because the tibia and femur are now in proper alignment, further degeneration of the knee joint is arrested and pain is reduced.

One such method and apparatus for performing tibial osteotomies is disclosed in U.S. Pat. Nos. 5,021,056 and 5,053,039, both issued to Hofmann, et al. The apparatus comprises, in part, a first guide assembly which grips the medial and lateral surfaces of the knee and serves to guide a saw blade in making the horizontal, or transverse, cut in the wedge. The first guide assembly is stabilized against the knee by at least two pins placed through the first guide assembly and into the head of the tibia. With the first guide assembly in place, a third hole in the first guide assembly is used to guide a drill bit completely through the head of the tibia adjacent to the location of the transverse cut. A depth gauge is then used to determine the width of the bone for the transverse cut. Below the stabilizing pins and the measurement hole, the first guide assembly includes a slot through which the saw blade must pass to make the transverse cut from the lateral side of the knee. Rather than cutting completely through the tibia head, however, the transverse cut is made such that an 8–10 millimeter bridge of cancellous bone is left on the medial side to act as a hinge during closure. The saw blade is then withdrawn from the transverse cut.

A second guide assembly is then placed at the site to provide guidance for the second, or oblique, cut. The second guide assembly includes a blade-shaped extension which is inserted into the transverse cut, and the guide is stabilized by the same two pins used for the first guide assembly. A plurality of oblique slots are formed into the second guide assembly which correspond to various angles for the oblique cut. The oblique slots are formed such that the end of the saw blade will meet with the end of the transverse cut previously made, thus enabling the cutting and removal of a wedge-shaped portion of bone from the tibia. After the wedge has been removed, the second guide assembly is removed from the osteotomy site.

To close the gap created by the removal of the wedge, an L-shaped plate is placed over the guide pins and across the portions of bone to be drawn together. The two guide pins are then removed and replaced by a pair of cancellous screws to hold the upper section of the plate against the bone surface. Next, a hole is drilled into the lateral tibia below the gap so that a ratcheted compression device can be employed to close the gap through plastic deformation of the medial bridge. One jaw of the compression device includes a rod which is inserted into the hole, while the other jaw includes a hook which engages the L-shaped plate. After the gap is closed, the compression device is removed, and additional cancellous screws are used to firmly attach the plate across the surgical wound.

While the Hofmann apparatus and method do appear to provide favorable results, there are several aspects to both the surgical procedure and the design of the components which allow the introduction of human error. For example, when the first guide assembly is placed across the knee, there is no way for the surgeon to obtain fluoroscopy images of the transverse cut. It may be possible for the first guide assembly to be constructed of a radiolucent material, but it would be more advantageous to dispense with this device in its entirety.

Second, after the transverse cut is made, the saw blade is removed from the cut so that the blade-shaped portion of the second guide assembly may be inserted. On occasion, the lower tibia must be slightly displaced, either to remove the saw blade or to fully insert the second guide assembly. This movement of the tibia will necessarily cause deformation of the medial bridge and can sometimes cause it to fracture. If the medial bridge is completely fractured, an additional plate may be required to keep the bones together, leading to significant healing complications and a possibility of loss of correction. Ideally, the tibial osteotomy should be performed with instruments that eliminate these concerns.

Third, once the wedge of bone has been removed, the guide pins are taken out of the tibia and replaced by cancellous screws to hold the L-shaped plate. While this procedure does not ordinarily cause problems, the screws may not accurately follow the hole left by the drill bit or the pins. In some instances, the screws may deviate away from the hole and push through the upper surface of the tibia head, because the operation is performed very close to the knee joint. Optimally, the screws which hold the plate to the tibia should use the drill bits or pins as a guide to verify that they will not harm other areas of the tibia.

SUMMARY OF THE INVENTION

It is therefore an object of this invention to provide an improved tibial osteotomy system that allows greater use of fluoroscopy imaging during surgery.

Another object of this invention is to provide an improved tibial osteotomy system that reduces trauma to the tibial bone tissue during surgery.

It is also an object of this invention to provide an improved tibial osteotomy system that uses a minimum of surgical instruments.

It is a further object of this invention to provide an improved tibial osteotomy system that minimizes the risks of fracturing the medial bridge.

Yet another object of this invention is to provide an improved tibial osteotomy system that is less sensitive to human error, and that reduces the possibility of misalignment of the instruments and fastening hardware.

Still another object of this invention is to provide an improved tibial osteotomy system that allows osteotomies to be performed more quickly than the prior art.

These and other objects and advantages of the present invention will no doubt become apparent to those skilled in the art after having read the following description of the preferred embodiment which are contained in and illustrated by the various drawing figures.

Therefore, in a preferred embodiment, a surgical kit for performing a tibial osteotomy is provided, comprising a pair of mounting pins for attaching an osteotomy guide in a predetermined relation to a tibia; an osteotomy guide, comprising a transverse slot, defining a transverse cutting plane, adapted to receive and guide a transverse cutting blade for making a transverse cut into the tibia, and a plurality of oblique slots angularly offset from the transverse slot, each oblique slot defining an oblique cutting plane, adapted to receive and guide an oblique cutting blade for making a selected oblique cut into the tibia, wherein the intersection of each oblique cutting plane with the transverse cutting plane defines a wedge of bone which may be removed from the tibia. Also included with the surgical kit are a compression clamp adapted to apply compressive forces to a first portion of the tibia above the transverse cut and to a second portion of the tibia below the oblique cut to draw the first and second portions together, and a fixation plate adapted to hold the portions of the tibia together during healing.

Also provided is a method for performing an upper tibial osteotomy, comprising the steps of temporarily holding an osteotomy guide, having mounting holes, in a desired orientation against the tibia; inserting mounting pins through the mounting holes and into the tibia; extending a first cutting blade through a first slot in the osteotomy guide; making a transverse cut through the tibia to a depth less than the depth of the tibia; allowing the first cutting blade to remain within the tibia after the transverse cut, and locking the osteotomy guide against the first cutting blade at a predetermined position on the first cutting blade; extending a second cutting blade through a second slot in the osteotomy guide; making an oblique cut through the tibia at an angle intersecting the transverse cut and severing a wedge-shaped portion of the tibia; removing the wedge-shaped portion to form a void in the tibia; drawing the sides of the tibia together to close the void; and applying a fixation plate to hold the tibia together.

BRIEF DESCRIPTION OF THE DRAWINGS

FIG. 1 is a perspective view of a preferred embodiment of the improved osteotomy guide used to perform a tibial osteotomy on the left leg.

FIG. 2 is a side elevation view of the osteotomy guide of FIG. 1.

FIG. 3 is a rear elevation view of the osteotomy guide of FIG. 1.

FIG. 4 is a sectional view taken along Section 4—4 showing the slanted end wall of the transverse slot.

FIG. 10 shows the step of making the transverse cut.

FIG. 11 shows the steps of locking the osteotomy guide in position with respect to the transverse saw blade and making the desired oblique cut.

DETAILED DESCRIPTION OF THE PREFERRED EMBODIMENT

Figure 6:
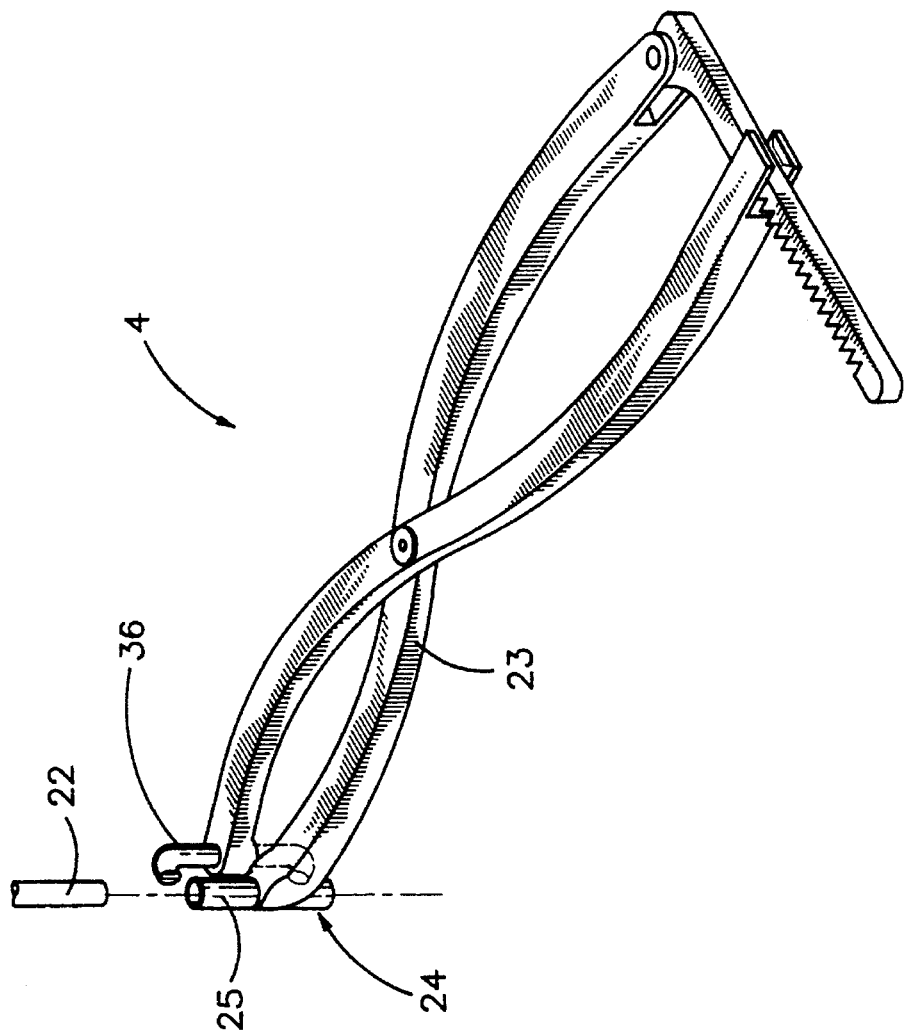
FIG. 6 is a perspective view of the clamp depicting the cylindrical jaw member.

In the drawings many details pertaining to fabrication and maintenance utility well established in the machine construction art and not bearing upon points of novelty are omitted in the interest of descriptive clarity and efficiency. Such details may include threaded connections, lockrings, shear pins, weld lines and the like. The spreading use of electron beam welding eliminates many such features and leaves no visible distinctive lines.

Turning now to FIGS. 1–8, the main components of the improved tibial osteotomy system are osteotomy guide 1, locking transverse saw blade 2, oblique saw blade 3, clamp 4, L-shaped plate 5, and cannulated screws 6. These components are discussed below with reference to the appropriate figures, after which a description will be provided of the improved method of performing the tibial osteotomy with reference to FIGS. 9 through 12.

With reference to FIGS. 1–3, osteotomy guide 1 is shown to comprise body 7 into which are formed a single transverse slot 8 and a plurality of guide slots 9. Transverse slot 8 is preferably open on one side of body 7 to accept transverse saw blade 2 without damaging the cutting edges on saw blade 2. In a preferred embodiment, the end wall 10 of transverse slot 8 is slanted away from saw blade 2, as shown in FIG. 4, in order to reduce the chances of damaging transverse saw blade 2 by reciprocating contact with body 7. Preferably, transverse slot 8 is wide enough in the plane of the transverse cut to accommodate the entire width of transverse saw blade 2, but only slightly larger in height than the thickness of transverse saw blade 2. This combination of dimensions for transverse slot 8 minimizes the vertical motion of the blade, provides a stable support for the blade, and enables a very straight transverse cut to be made through the tibia. Transverse slot 8 is formed parallel to the top surface of body 7 and is vertically offset below the top surface by about 20 mm. At least two sharp protrusions 20 are located on the inside face 21 of osteotomy guide 1 which can assist in establishing stable contact between the tibia and the osteotomy guide during placement of the drill bits or pins 22, as well as during both the transverse cut and the oblique cut.

Preferably, body 7 includes at least eight oblique slots 9 angularly spaced from transverse slot 8 and from one another such that the oblique cutting plane corresponding to each of oblique slots 9 intersects the transverse cutting plane at a predetermined point A, best shown in FIG. 11. Oblique slots 9 are spaced about two degrees (2°) apart and allow for six degrees (6°) to twenty degrees (20°) of bone material to be removed. The internal dimensions of each oblique slot 9, including the presence of slanted end walls, are completely analogous to the dimensions of transverse slot 8, although such dimensions are to be considered with respect to the plane of the particular oblique cut to which each oblique slot 9 corresponds. The removal of bone wedges 26 within the 6°–20° range corresponds directly to the degree of correction desired by the surgeon. For tibial osteotomies which are performed on the left knee from a lateral direction, it is preferred that both the transverse slot 8 and the oblique slots 9 open toward the left side of the osteotomy guide 1. Likewise, for those osteotomies which are performed on the right knee from a lateral direction, the transverse and oblique slots 8,9, respectively, should be open toward the right side of the osteotomy guide 1.

In order for the transverse and oblique cuts to intersect at their distal extremes, it is essential that there be a fixed length between body 7 and the distal extreme of the transverse cut. The present invention accomplishes this by a unique interaction between transverse saw blade 2 and locking means 11. Locking means 11 is any structure which can retain transverse saw blade 2 in a temporarily fixed position with respect to body 7. By way of example, locking means 11 may simply comprise a threaded or non-threaded hole 12 formed into the top of body 7 and perpendicularly through transverse slot 8 into which a screw or pin 13 may be inserted. When transverse saw blade 2 is located within transverse slot 8, pin 13 is also matable with a corresponding hole 14 formed into transverse saw blade 2, as will be explained shortly herein. As an alternative to the hole 14 in transverse saw blade 2, pin 13 may also take the form of a set screw tightened against a predetermined location on saw blade 2. Such an alternative embodiment would not be preferred, however, because it lacks the consistency and predictability of the preferred embodiment.

Figure 14:
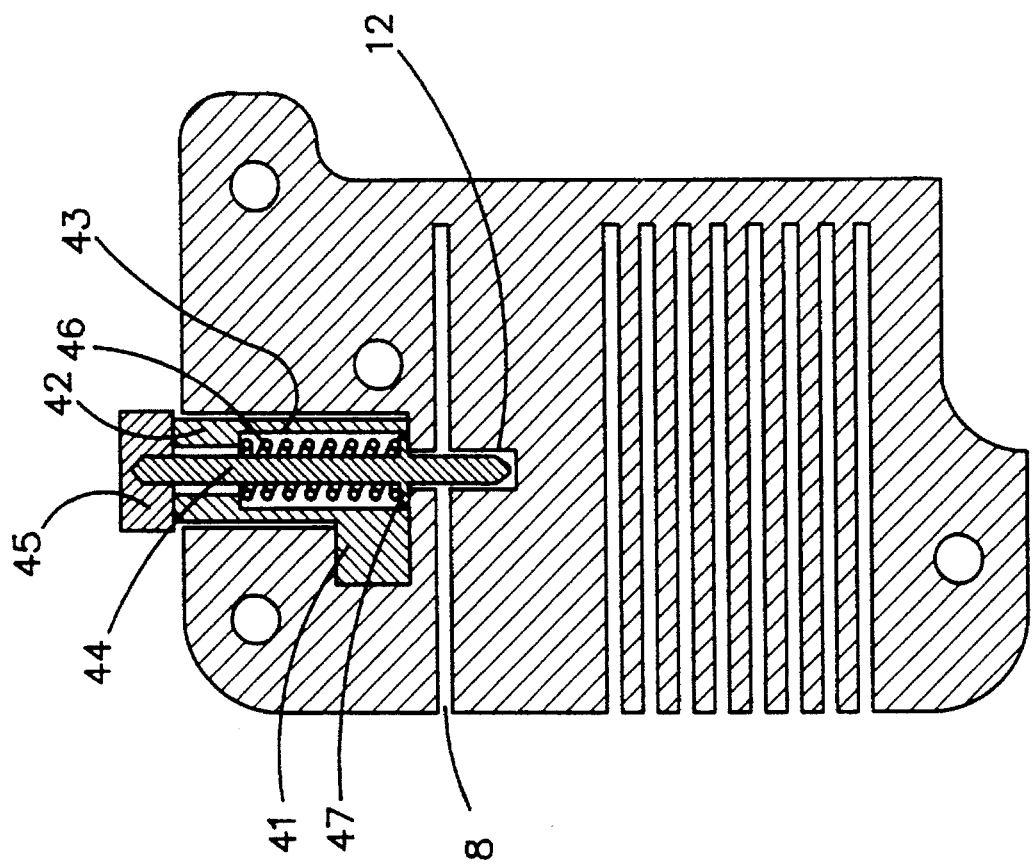
FIG. 14 is a sectional view of the osteotomy guide and locking means of FIG. 13.
Figure 13:
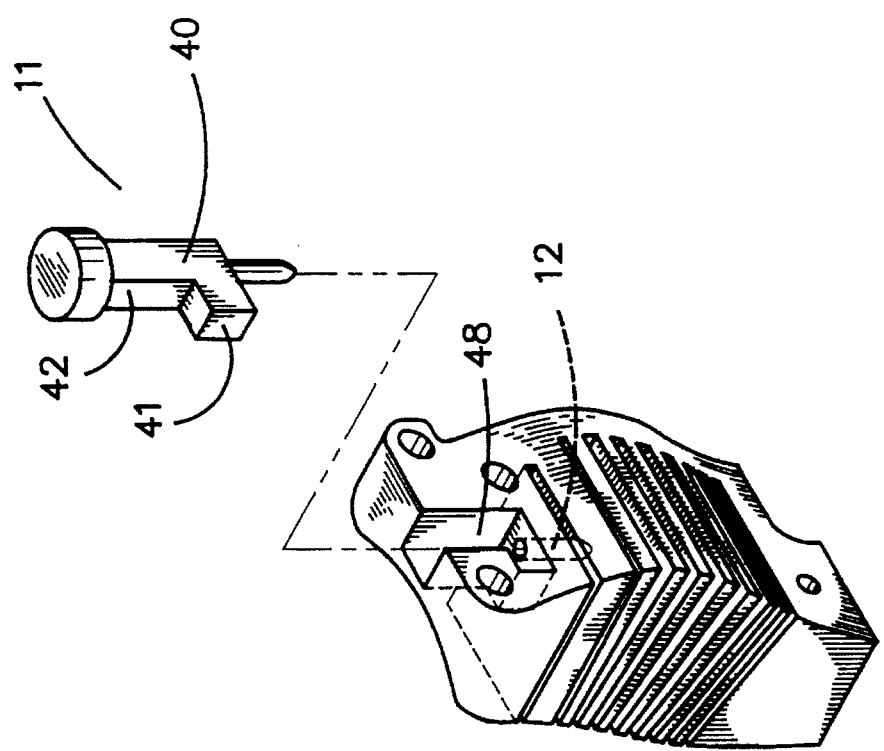
FIG. 13 depicts an alternative embodiment of the locking means for the osteotomy guide.

A further alternative embodiment of locking means 11 is depicted in FIGS. 13 and 14, which affords a quick release feature for ease of use in a surgical environment. An L-shaped member 40 is provided with a horizontal portion 41 and a vertical portion 42, and a vertical passageway 43 is formed through vertical portion 42. Insertion member 44 is slidably disposed within passageway 43 and is retained therein by a combination of cap 45, which is attached to the upper end of insertion member 44, and compression spring 46. Spring 46 is retained within passageway 43 by annular flange 47 formed on insertion member 44. The interaction of insertion member 44 and spring 46 is such that spring 46 urges the lowermost tip of insertion member 44 away from L-shaped member 40 at all times. Insertion member 44 can thus be completely retracted by an upward force on cap 45 which compresses spring 46. As shown in FIG. 13, an L-shaped aperture 48 is formed into body 7 to accommodate the presence of L-shaped member 40. When the osteotomy guide 1 is ready to be locked into position with respect to transverse saw blade 2, cap 45 is pulled upward to retract insertion member 44. As the L-shaped member 40 is moved into L-shaped aperature 48, insertion member 44 snaps down into holes 12,14 in body 7 and transverse saw blade 2, respectively. To release the osteotomy guide 1, the reverse operation is performed. In this manner, the necessary locking and unlocking operations can be accomplished in a very short amount of time and with very little difficulty.

Guide holes 15,16 are also formed through the upper portion of body 7 in a plane substantially parallel to and above transverse slot 8. Guide holes 15,16 initially serve as guides for drill bits or pins 22 placed into the tibial head, but also serve as the means for holding and stabilizing osteotomy guide 1 on the drill bits or pins 22 once they are in place. Measurement guide hole 17 is also formed into body 7 parallel to guide holes 15,16, but it is located directly adjacent to transverse slot 8. Measurement guide hole 17 should be as close to transverse slot 8 as possible so that an accurate measurement of tibial width at the transverse cut level may be made. Finally, reference guide hole 19 is formed into the bottom portion of body 7 so that an additional drill bit or pin 22 can be guided into the tibia for extra stability or for a reference point. The reference hole created in the tibia is also very useful in realigning osteotomy guide 1 in the event that additional bone must be removed from the tibia if greater correction is desired.

Figure 5A:
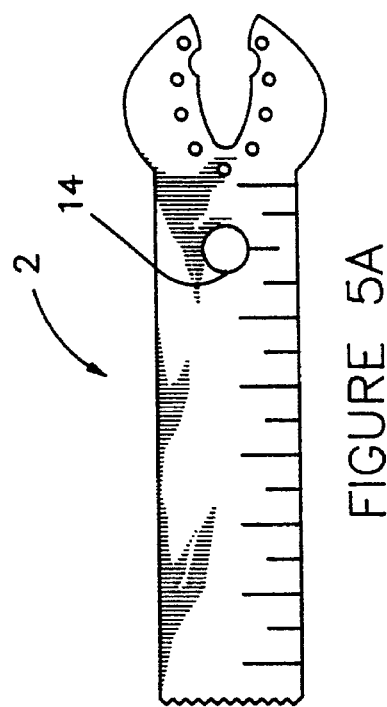
FIG. 5A is a top view of the transverse saw blade.
Figure 5B:
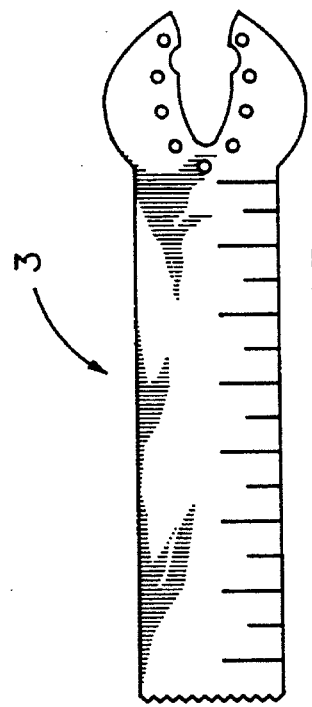
FIG. 5B is a top view of the oblique saw blade.

With respect to FIGS. 5A and 5B, the details of the transverse and oblique saw blades 2,3 are shown. Oblique saw blade 3 may simply be any one of a number of commercially available saw blades used for such purposes. Transverse saw blade 2 is identical in every respect to oblique saw blade 3, except for the presence of hole 14 described earlier herein. Hole 14 should be formed far enough from the cutting edges of transverse saw blade 2 to accommodate the majority of tibial widths seen in practice. Of course, locations for hole 14 which are outside this range may be required in cases of very small or very large tibial widths. If desired, a second transverse saw blade 2 may actually be used to make the oblique cut, because the presence of hole 14 does not affect its cutting ability.

As can be seen from FIG. 6, compression clamp 4 is identical in most respects to the compression clamp disclosed in the prior art. However, one jaw member 23 of clamp 4 of the present invention includes means 24 for gripping a drill bit 22 placed into the bone. Gripping means 24 may simply comprise a cylinder 25 attached to jaw member 23 which slides over the drill bit 22 when the gap 27 is to be closed. Alternatively, gripping means 24 may also be a half-cylinder which surrounds the underside of drill bit 22. The key advantage to such designs is that the drill bit 22 may be left within the tibia, rather than removing it and inserting a second instrument. The result is a quicker operation, less trauma to the bone tissue, and more even distribution of force during compression.

Figure 7:
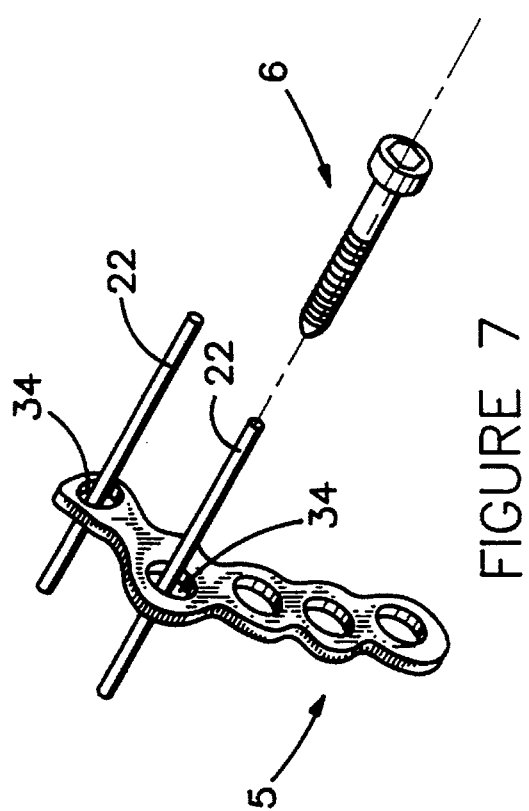
FIG. 7 is a perspective view of the L-shaped plate, cannulated screw, and drill bits.
Figure 8:
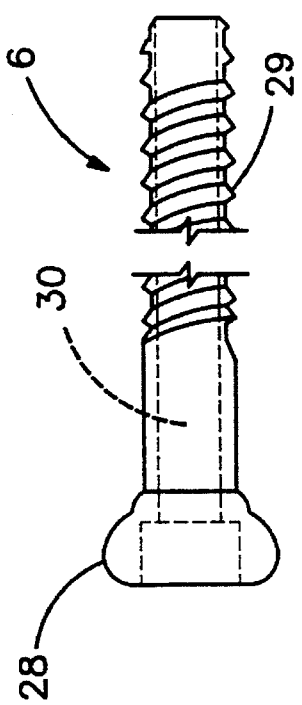
FIG. 8 is a side elevation view of a cannulated screw showing the internal passageway.

In the improved tibial osteotomy system, cannulated screws 6 are used to fasten L-shaped plate 5, shown in more detail in FIG. 7, over the closed gap 27 after removal of the wedge 26. FIG. 8 indicates that cannulated screws 6 are characterized by a head 28 and a threaded shank 29 in the same manner as those screws seen in the art. However, each cannulated screw 6 includes a passageway 30 formed completely through the threaded shank 29. By virtue of passageway 30, cannulated screws 6 can be placed into the tibia directly over the drill bits or pins 22, thereby using those pins 22 as a guide for proper alignment of the screws 6. Once the cannulated screws 6 have been inserted, the pins 22 can be removed.

Operation of the improved tibial osteotomy system is simple and is described with reference to FIGS. 9 through 12. Once the degree of correction is determined through clinical, radiological, and/or mechanical evaluation, the knee joint 31 is exposed by incision as known in the art. A Keith needle, or K-wire 32, is then introduced under the lateral meniscus within the knee joint 31 to identify the joint line. Next, the osteotomy guide 1 is placed against the tibia such that the top surface of body 7 touches the K-wire 32, and such that it is centered on the lateral plateau in the lateral view. With the osteotomy guide 1 in correct vertical and horizontal placement with respect to the joint line, the angular orientation in the lateral view is checked to verify that the transverse slot 8 is parallel to the posterior slope of the knee joint 31. Drill bits 22 are then drilled through guide holes 15,16 into the tibial head parallel to the proximal tibial plateau in the anterior view. Standard fluoroscopic imaging techniques can be employed to verify that the drill bits 22 are entered in a parallel fashion.

Figure 9:
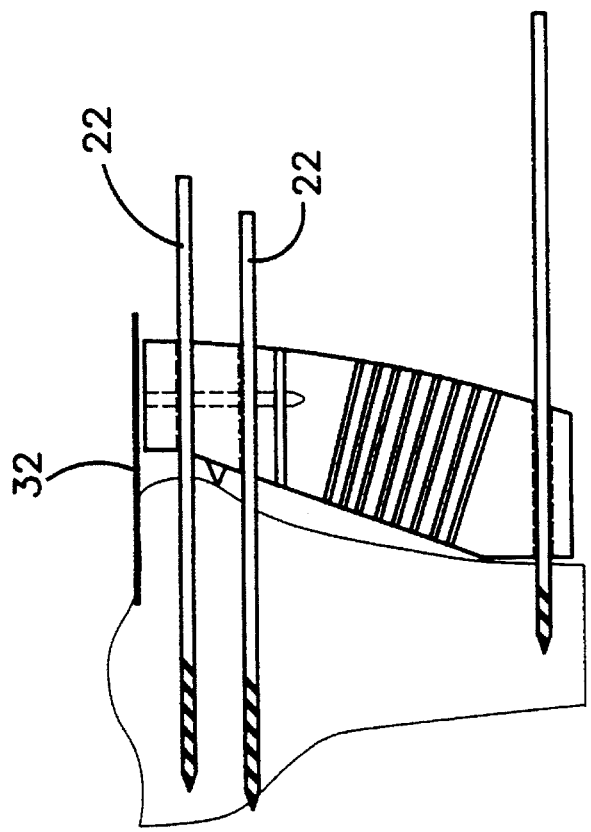
FIG. 9 shows a tibia with the K-wire inserted and the osteotomy guide supported by the drill bits.

A third drill bit 22 having metric gradations inscribed thereon is then drilled through the tibia head using the measurement guide hole 17 in body 7. The third drill bit 22 is advanced through the medial side of the tibia until it begins to protrude from the bone. Given the known thickness of the osteotomy guide 1 at the level of measurement guide hole 17 and any space in between guide 1 and the tibial bone surface, the thickness of the tibia at the site of the transverse cut can be easily determined by reading the gradations on drill bit 22 and subtracting the thickness of the osteotomy guide 1 and any space between the guide 1 and the tibia. As an alternative to drill bits 22, pins having metric gradations may be hammer-driven through the tibia with the same effect. Furthermore, the tibial thickness may also be measured using the measurement probe disclosed in the Hofmann reference. Optionally, a reference hole is then created in the cortical bone using either a drill bit or pin 22 guided by the reference guide hole 19, as shown in FIG. 9.

Now that the osteotomy guide 1 is stabilized against the tibia, the transverse saw blade 2 is used to make the transverse cut through transverse slot 8, as shown in FIG. 10. The depth of the transverse cut is such that an 8–10 mm medial bridge 33 (shown in FIG. 11) remains intact. Rather than remove the transverse saw blade 2, the motorized base is disengaged, and the osteotomy guide 1 is slid back along the guide pins 22 until the hole 14 on the transverse saw blade 2 becomes aligned with the hole 12 in body 7. Pin 13 is then inserted through hole 12 to lock the position of the osteotomy guide 1 with respect to the transverse saw blade 2 as in FIG. 11. With the osteotomy guide 1 in the locked position, the oblique slots 9 are now oriented for the oblique cut. Oblique saw blade 3 is then used to make the selected oblique cut through the oblique slot 9 corresponding to the desired degree of correction. The end of oblique saw blade 3 should meet the end of transverse saw blade 2 at point A in order to completely cut the wedge of bone 26 to be removed. After the oblique cut is made, the osteotomy guide 1 and transverse saw blade 2 are removed from guide pins 22, and the wedge 26 of bone is removed from the tibia.

Figure 12:
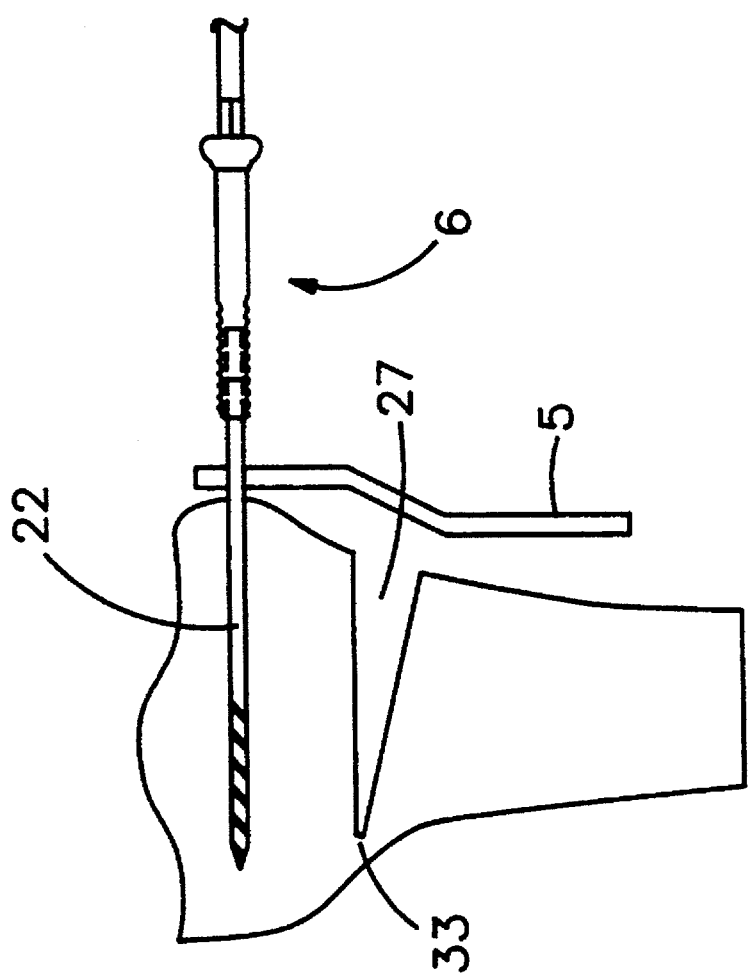
FIG. 12 shows the step of inserting the cannulated screws over the guide pins to secure the L-shaped plate across the osteotomy site.

The gap 27 resulting from the removal of wedge 26 is closed in the following manner. With the guide pins 22 still seated within the tibial head, the L-shaped plate 5 is placed over the pins 22 through a corresponding pair of holes 34 in plate 5, as shown in FIGS. 7 and 12. The particular design of plate 5 is substantially as described in the above mentioned Hofmann patents, which portion of those disclosures is incorporated herein by reference. Cannulated screws 6 are then placed over guide pins 22 and through holes 34 to loosely fasten plate 5 to the tibia. As explained earlier herein, the presence of guide pins 22 through passageway 30 serve to prevent any deviation of cannulated screws 6 from their intended path. Thus, there is no danger of protrusion of the screws 6 through the upper joint surface. The hook portion 36 on compression clamp 4 is then caused to engage one of the remaining holes in plate 5, and the jaw member 23 having the cylinder 25 is placed against an area of cortical bone. Another drill bit 22 is drilled into the cortical bone using the cylinder 25 as a guide. Once the clamp 4 is securely attached across the gap 27, the clamp 4 is gradually tightened through each successive ratcheted position until the gap 27 is fully closed by plastically deforming the medial bridge 33. Finally, cortical screws are used in the available holes in plate 5 to secure the lower portion of plate 5 to the tibia, while the cannulated screws 6 are tightened through holes 34. Cleaning and closure of the surgical wound is then accomplished through methods known in the art.

Although the present invention has been described in terms of specific embodiments, it is anticipated that alterations and modifications thereof will no doubt become apparent to those skilled in the art. It is therefore intended that the following claims be interpreted as covering all such alterations and modifications as fall within the true spirit and scope of the invention.

I claim:

1. A surgical kit for performing a tibial osteotomy, comprising:
   (a) an osteotomy guide, comprising:
      (i) mounting means for attaching the guide in a predetermined relation to a tibia;
      (ii) a transverse slot, defining a transverse cutting plane, adapted to receive and guide a transverse cutting blade for making a transverse cut into said tibia; and
      (iii) a plurality of oblique slots angularly offset from said transverse slot, each said oblique slot defining an oblique cutting plane, adapted to receive and guide an oblique cutting blade for making a selected oblique cut into said tibia, wherein the intersection of each of said oblique cutting planes with said transverse cutting plane is adapted to define a wedge of bone which may be removed from said tibia;
   (b) a transverse cutting blade adapted to pass through said transverse slot;
   (c) fixation means for holding surfaces of said tibia created by said transverse cut and said oblique cut together during the healing of said tibia; and
   (d) locking means on said osteotomy guide for lockably engaging said transverse cutting blade and positioning said osteotomy guide at a predetermined location relative to said transverse cutting blade.

2. The surgical kit of claim 1, wherein said mounting means comprises:
   (a) at least two pins for placement into said tibia;
   (b) at least two holes formed into said osteotomy guide adapted to receive said pins.

3. The surgical kit of claim 1, wherein said osteotomy guide further includes a measurement guide hole adjacent to said transverse slot and adapted to receive a drill pin.

4. The surgical kit of claim 1, wherein said transverse cutting blade includes a first locking hole formed therethrough; and wherein said locking means on said osteotomy guide includes a second locking hole formed across said transverse slot, and a locking member removably insertable through said first and second locking holes.

5. The surgical kit of claim 4, wherein said locking member is a spring-loaded pin.

6. The surgical kit of claim 1, wherein the angular offset of said oblique slots from said transverse slot ranges from about six degrees to about twenty degrees.

7. The surgical kit of claim 1, wherein said osteotomy guide further includes a plurality of protrusions sufficient to establish stable contact of said osteotomy guide against the tibia.

8. The surgical kit of claim 1, further comprising clamping means for applying compressive forces to a first portion of the tibia above said transverse cut and to a second portion of the tibia below said oblique cut to draw said surfaces together; and wherein said clamping means includes at least one cylindrical member adapted to slide over a pin placed into said second portion of said tibia.

9. A method for performing an upper tibial osteotomy, comprising the steps of:
  (a) providing a transverse cutting blade and an osteotomy guide, wherein said osteotomy guide comprises:
    (i) mounting means for attaching the guide in a predetermined relation to a tibia, said tibia having a depth;
    (ii) a transverse slot, defining a transverse cutting plane, adapted to receive and guide said transverse cutting blade;
    (iii) a plurality of oblique slots angularly offset from said transverse slot, each said oblique slot defining an oblique cutting plane, adapted to receive and guide an oblique cutting blade for making a selected oblique cut into said tibia, wherein the intersection of each of said oblique cutting planes with said transverse cutting plane is adapted to define a wedge of bone which may be removed from said tibia; and
    (iv) locking means for lockably engaging said transverse cutting blade and positioning said osteotomy guide at a predetermined location relative to said transverse cutting blade;
  (b) placing said osteotomy guide against said tibia;
  (c) extending said transverse cutting blade through said transverse slot;
  (d) making a transverse cut through said tibia to a distance less than the depth of said tibia;
  (e) extending an oblique cutting blade through one of said plurality of oblique slots;
  (f) making an oblique cut through said tibia at an angle intersecting said transverse cut and severing a wedge-shaped portion of said tibia;
  (g) removing said wedge-shaped portion to form a void in said tibia, said void being defined by an upper side, created by said transverse cut, and a lower side, created by said oblique cut; and
  (h) drawing said upper and lower sides of said tibia together and permanently closing said void.

10. The method of claim 9, further comprising the steps of, after making said transverse cut and prior to making said oblique cut, allowing said transverse cutting blade to remain within said tibia, and locking said osteotomy guide against said transverse cutting blade at a predetermined location relative to said transverse cutting blade.

11. The method of claim 9, wherein said osteotomy guide includes at least two mounting holes, and wherein the placing of said osteotomy guide against said tibia comprises the steps of:
  (a) temporarily holding said osteotomy guide in a desired orientation against said tibia; and
  (b) inserting at least two mounting pins through said mounting holes and into said tibia.

12. The method of claim 11, wherein the step of permanently closing said void comprises the step of applying a fixation plate to hold said tibia together.

* * * * *